(12) United States Patent
Asahi et al.

(10) Patent No.: US 9,204,890 B2
(45) Date of Patent: Dec. 8, 2015

(54) FLUID EJECTION DEVICE

(71) Applicant: SEIKO EPSON CORPORATION, Tokyo (JP)

(72) Inventors: Tsunemori Asahi, Azumino (JP); Masaki Gomi, Hino (JP)

(73) Assignee: SEIKO EPSON CORPORATION, Tokyo (JP)

(*) Notice: Subject to any disclaimer, the term of this patent is extended or adjusted under 35 U.S.C. 154(b) by 0 days.

(21) Appl. No.: 14/682,819

(22) Filed: Apr. 9, 2015

(65) Prior Publication Data
US 2015/0290933 A1 Oct. 15, 2015

(30) Foreign Application Priority Data
Apr. 10, 2014 (JP) .................. 2014-080826

(51) Int. Cl.
*B41J 29/38* (2006.01)
*A61B 17/3203* (2006.01)
(52) U.S. Cl.
CPC .................. *A61B 17/3203* (2013.01)
(58) Field of Classification Search
CPC .................................. A61B 17/3203
See application file for complete search history.

(56) References Cited

U.S. PATENT DOCUMENTS

| 5,259,842 A * | 11/1993 | Plechinger et al. ......... 604/152 |
| 5,505,729 A * | 4/1996 | Rau .................. 606/40 |
| 5,871,462 A * | 2/1999 | Yoder et al. ............. 604/22 |
| 2009/0043480 A1 * | 2/2009 | Seto et al. ............. 701/103 |
| 2009/0314314 A1 * | 12/2009 | Klein et al. ............. 134/32 |
| 2010/0078495 A1 * | 4/2010 | Seto et al. ............. 239/1 |
| 2011/0036859 A1 * | 2/2011 | Matsuzaki et al. ............. 222/1 |
| 2011/0054505 A1 * | 3/2011 | Kojima et al. ............. 606/167 |
| 2011/0194945 A1 * | 8/2011 | Kensy et al. ............. 417/26 |
| 2011/0208224 A1 * | 8/2011 | Kojima ............. 606/167 |
| 2012/0176431 A1 * | 7/2012 | Kojima ............. 347/14 |
| 2013/0158544 A1 * | 6/2013 | Kuhner et al. ............. 606/39 |
| 2014/0296892 A1 * | 10/2014 | Uchida et al. ............. 606/167 |

FOREIGN PATENT DOCUMENTS

JP 2013-213422 A 10/2013

* cited by examiner

*Primary Examiner* — Julian Huffman
(74) *Attorney, Agent, or Firm* — Maschoff Brennan

(57) ABSTRACT

A fluid ejection device includes a fluid ejection unit that ejects a fluid and an ejection control unit that controls ejection of the fluid. A fluid container accommodates the fluid supplied to the fluid ejection unit. A pressure adjustment unit adjusts an inner pressure of the fluid container such that the inner pressure gets closer to a target pressure than a first threshold value. The ejection control unit has first and second ejection modes. In the first ejection mode, when the inner pressure is closer to the target pressure than a second threshold value separated from the target pressure farther than the first threshold value, the ejection control unit receives a demand for ejection of fluid. In the second ejection mode, even when the inner pressure is not closer to the target pressure than the second threshold value, the ejection control unit receives a demand for ejection of fluid.

8 Claims, 8 Drawing Sheets

FLUID EJECTION DEVICE

This application claims the benefit of Japanese Patent Application No. 2014-080826 filed, on Apr. 10, 2014. The content of the aforementioned application is incorporated herein by reference in its entirety.

BACKGROUND

1. Technical Field

The present invention relates to a fluid ejection device.

2. Related Art

A fluid ejection device for medical purposes that can incise and excise living tissue by ejecting a fluid has been developed. JP-A-2013-213422 is an example of the related art.

In the fluid ejection device, in a case where a certain amount of time is required so as to increase pressure to an amount of pressure at which a fluid can be ejected, a user waits idly, and has difficulty in efficiently expediting an operation or the like. In contrast, even when a fluid pressure is separated from a target pressure, the fluid is required to be ejected while a control operation is performed so as to reduce an amount of time taken to the ejection of the fluid.

SUMMARY

An advantage of some aspects of the invention is to be able to eject a fluid while performing a control operation of reducing an amount of time taken to the ejection of the fluid, even when a fluid pressure is separated from a target pressure.

A fluid ejection device according to an aspect of the invention includes: a fluid ejection unit that ejects a fluid; an ejection control unit that controls the ejection of the fluid from the fluid ejection unit; a fluid container that accommodates the fluid to be supplied to the fluid ejection unit; and a pressure adjustment unit that adjusts an inner pressure of the fluid container in such a manner that the inner pressure of the fluid container gets closer to a target pressure than a first threshold value for the inner pressure of the fluid container. The ejection control unit has a first ejection mode and a second ejection mode as ejection modes, and in the first ejection mode, when the inner pressure of the fluid container is closer to the target pressure than a second threshold value separated from the target pressure further than the first threshold value, the ejection control unit receives a demand for the ejection of the fluid, and in the second ejection mode, even when the inner pressure of the fluid container is not closer to the target pressure than the second threshold value, the ejection control unit receives a demand for the ejection of the fluid.

Other features of the invention will be made apparent by the description of this specification and the accompanying drawings.

BRIEF DESCRIPTION OF THE DRAWINGS

The invention will be described with reference to the accompanying drawings, wherein like numbers reference like elements.

DESCRIPTION OF EXEMPLARY EMBODIMENTS

Figure 1:
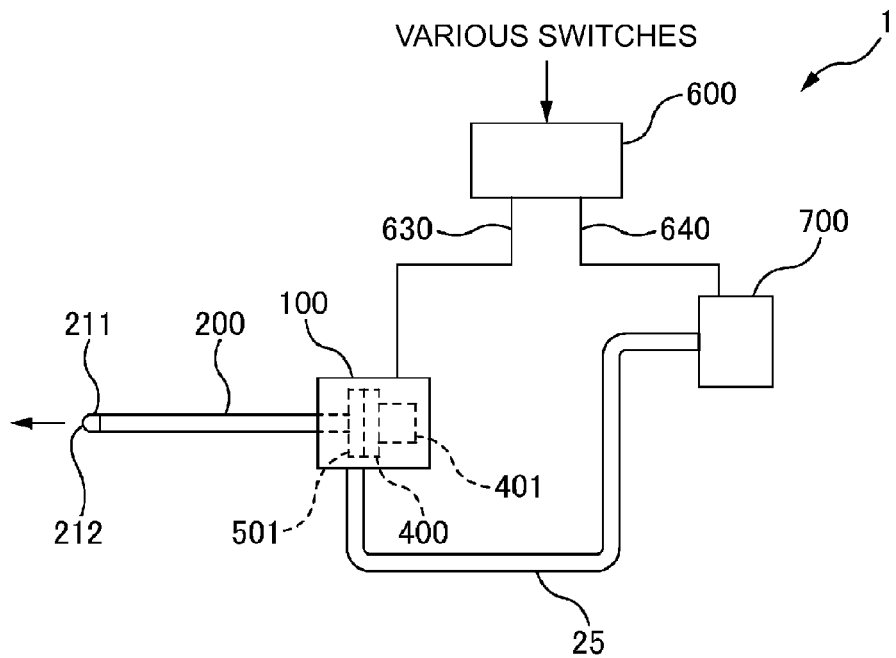
FIG. 1 is a view illustrating the configuration of a fluid ejection device as an operation scalpel according to an embodiment.

At least the following facts are apparent from this specification and the accompanying drawings.

An aspect of the invention is directed to a fluid ejection device including: a fluid ejection unit that ejects a fluid; an ejection control unit that controls the ejection of the fluid from the fluid ejection unit; a fluid container that accommodates the fluid to be supplied to the fluid ejection unit; and a pressure adjustment unit that adjusts an inner pressure of the fluid container in such a manner that the inner pressure of the fluid container gets closer to a target pressure than a first threshold value for the inner pressure of the fluid container. The ejection control unit has a first ejection mode and a second ejection mode as ejection modes, and in the first ejection mode, when the inner pressure of the fluid container is closer to the target pressure than a second threshold value separated from the target pressure further than the first threshold value, the ejection control unit receives a demand for the ejection of the fluid, and in the second ejection mode, even when the inner pressure of the fluid container is not closer to the target pressure than the second threshold value, the ejection control unit receives a demand for the ejection of the fluid.

In this manner, in the first ejection mode, when the inner pressure of the fluid container is adjusted so as to get closer to the target pressure than the first threshold value, and the inner pressure is closer to the target pressure than the second threshold value, the ejection control unit receives a demand for the ejection of the fluid, and thereby it is possible to reduce an amount of time taken from the reception of the demand for the ejection of the fluid to the ejection of the fluid. In contrast, in the second ejection mode, even when the inner pressure of the fluid container is adjusted so as to get closer to the target pressure than the first threshold value, and the inner pressure is not closer to the target pressure than the second threshold value, the ejection control unit receives a demand for the ejection of the fluid, and thereby it is possible to eject the fluid even at a pressure separated from the target pressure.

It is preferable that the fluid ejection device further includes a reporting device configured to report that the ejection control unit receives a demand for the ejection of the fluid in the second ejection mode.

In this manner, when the ejection control unit receives a demand for the ejection of the fluid in the second ejection mode, it is possible to report that the fluid is ejected in the second ejection mode, and thereby a user can recognize that the fluid is ejected in a state where the inner pressure of the fluid container is not closer to the target pressure than the first threshold value.

It is preferable that the fluid ejection device further includes a switch that switches an ejection mode between the first ejection mode and the second ejection mode.

In this manner, a user can clearly switch the ejection mode between the first ejection mode and the second ejection mode.

In the fluid ejection device, it is preferable that, when the inner pressure of the fluid container is not closer to the target pressure than the second threshold value, the ejection mode is switched to the second ejection mode.

In this manner, when the inner pressure of the fluid container is not closer to the target pressure than the second threshold value, it is possible to switch the ejection mode to the second ejection mode.

In the fluid ejection device, it is preferable that, after at least one of an operation of filling the fluid ejection unit with the fluid, a deaeration operation of the fluid ejection unit, and a fluid ejection intensity change operation of the fluid ejection unit is performed, the ejection mode is switched to the second ejection mode.

In this manner, when the setting of the fluid ejection device is changed, or an initial operation of the fluid ejection device is performed, it is possible to eject the fluid in a trial mode by controlling the fluid ejection device in the second ejection mode.

In the fluid ejection device, it is preferable that, in a state where the inner pressure of the fluid container is lower than the target pressure, when the inner pressure of the fluid container is separated from the target pressure by the second threshold value or greater, the pressure adjustment unit performs a first pressure increase control operation in which the pressure adjustment unit increases the inner pressure by reducing the inner volume of the fluid container by a first amount, and when the inner pressure of the fluid container is closer to the target pressure than the second threshold value, and is separated from the target pressure by the first threshold value or greater, the pressure adjustment unit performs a second pressure increase control operation in which the pressure adjustment unit increases the inner pressure by reducing the inner volume of the fluid container by a second amount less than the first amount.

In this manner, when the inner pressure of the fluid container is separated from the target pressure by the second threshold value or greater, it is possible to increase the inner pressure to become closer to the target pressure by reducing the inner volume of the fluid container by the first amount. In contrast, when the inner pressure of the fluid container is closer to the target pressure than the second threshold value, and is separated from the target pressure by the first threshold value or greater, it is possible to more finely increase the inner pressure by reducing the inner volume of the fluid container by a second amount less than the first amount.

It is preferable that the fluid ejection device further includes a connection channel that connects the fluid ejection unit and the fluid container, and acts as a channel through which the fluid flows, and an opening and closing unit that is controlled to open and close the connection channel by the pressure adjustment unit, and when the ejection control unit receives a demand for the ejection of the fluid, the pressure adjustment unit controls the opening and closing unit to open the connection channel, and stops the adjustment of the inner pressure of the fluid container.

In this manner, it is possible to supply the fluid to the fluid ejection unit by opening the connection channel between the fluid ejection unit and the fluid container, and to eject the fluid by receiving the demand for the ejection of the fluid.

In the fluid ejection device, it is preferable that, when the ejection control unit receives a demand for the ejection of the fluid, the pressure adjustment unit supplies the fluid to the fluid ejection unit by controlling the opening and closing unit to open the connection channel and reducing the inner volume of the fluid container by a predetermined amount each time.

In this manner, when the fluid is ejected from the fluid ejection unit, it is possible to send a predetermined amount of the fluid to the fluid ejection unit without controlling the inner pressure of the fluid container.

Embodiment

Hereinafter, an embodiment of the invention will be described with reference to the accompanying drawings. A fluid ejection device according to the embodiment can be used in various procedures such as the cleaning or cutting of a fine object or structure, living tissue, or the like; however, an example of the embodiment given in the following description is the fluid ejection device suitable for use as an operation scalpel to incise or excise living tissue. Accordingly, a fluid used in the fluid ejecting device according to the embodiment is water, physiologic saline, a predetermined fluid medicine, or the like. The drawings referenced in the following description are schematic views in which a portion or a member is vertically and horizontally scaled differently from an actual scale for illustrative purposes.

Entire Configuration

FIG. 1 is a view illustrating the configuration of a fluid ejection device 1 as an operation scalpel according to the embodiment. The fluid ejection device 1 includes a pump 700 for supplying a fluid; a pulsation generator (equivalent to a fluid ejection unit) 100 that converts the form of the fluid supplied from the pump 700 into a pulsed flow, and ejects a pulsed flow of the fluid; a drive control unit (equivalent to an ejection control unit) 600 that controls the fluid ejection device 1 in cooperation with the pump 700; and a connection tube (equivalent to a connection channel) 25 as a connection path through which the pump 700 and the pulsation generator 100 are connected to each other, and the fluid flows.

The pulsation generator 100 includes a fluid chamber 501 that accommodates the fluid supplied from the pump 700; a diaphragm 400 that changes the volume of the fluid chamber 501; and a piezoelectric element 401 that vibrates the diaphragm. 400, all of which will be described later in detail.

The pulsation generator 100 includes a thin pipe-like fluid ejection tube 200 that acts as a channel of the fluid discharged from the fluid chamber 501, and a nozzle 211 that is mounted on a tip end portion of the fluid ejection tube 200 and has a reduced channel diameter.

The pulsation generator 100 converts a form of the fluid into a pulsed flow and ejects a pulsed flow of the fluid at high speed via the fluid ejection tube 200 and the nozzle 211 by driving the piezoelectric element 401 in response to drive signals output from the drive control unit 600, and changing the volume of the fluid chamber 501.

The drive control unit 600 and the pulsation generator 100 are connected to each other via a control cable 630, and drive signals for driving the piezoelectric element 401 are output from the drive control unit 600 and are transmitted to the pulsation generator 100 via the control cable 630.

The drive control unit 600 and the pump 700 are connected to each other via a communication cable 640, and the drive control unit 600 and the pump 700 transmit and receive various commands or data therebetween according to a predetermined communication protocol such as a controller area network (CAN).

The drive control unit 600 receives signals from various switches operated by a practitioner who performs an operation using the pulsation generator 100, and controls the pump 700 or the pulsation generator 100 via the control cable 630 or the communication cable 640.

The switches that input signals to the drive control unit 600 are a pulsation generator start-up switch, an ejection intensity switching switch, a flushing switch, and the like (not illustrated).

The pulsation generator start-up switch (not illustrated) is a switch for switching a state of ejection of the fluid from the pulsation generator 100 between an ejection mode and a non-ejection mode. When a practitioner who performs an operation using the pulsation generator 100 operates the pulsation generator start-up switch (not illustrated), the drive control unit 600 controls the pulsation generator 100 to eject the fluid or stop the ejection of the fluid in cooperation with the pump 700. The pulsation generator start-up switch (not illustrated) can be a switch configured to be operated by the practitioner's feet, or a switch that is provided integrally with the pulsation generator 100 grasped by the practitioner, and configured to be operated by the practitioner's hands or fingers.

The ejection intensity switching switch (not illustrated) is a switch for changing the intensity of fluid ejection from the pulsation generator 100. When the ejection intensity switching switch (not illustrated) is operated, the drive control unit 600 controls the pulsation generator 100 and the pump 700 so as to increase and decrease the intensity of fluid ejection.

The flushing switch (not illustrated) will be described later.

In the embodiment, a pulsed flow implies a flow of a fluid, a flow direction of which is constant, and the flow rate or flow speed of which is changed periodically or non-periodically. The pulsed flow may be an intermittent flow in which the flowing and stopping of the fluid are repeated; however, since the flow rate or flow speed of the fluid is preferably changed periodically or non-periodically, the pulsed flow is not necessarily an intermittent flow.

Similarly, the ejection of a fluid in a pulsed form implies the ejection of the fluid by which the flow rate or moving speed of an ejected fluid is changed periodically or non-periodically. An example of the pulsed ejection is an intermittent ejection by which the ejection and non-ejection of a fluid are repeated; however, since the flow rate or moving speed of an ejected fluid is preferably changed periodically or non-periodically, the pulsed ejection is not necessarily an intermittent ejection.

When the driving of the pulsation generator 100 is stopped, that is, when the volume of the fluid chamber 501 is not changed, the fluid supplied from the pump 700 as a fluid supply unit at a predetermined pressure continuously flows out of the nozzle 211 via the fluid chamber 501.

The fluid ejection device 1 according to the embodiment may be configured to include a plurality of the pumps 700.

Figure 2:
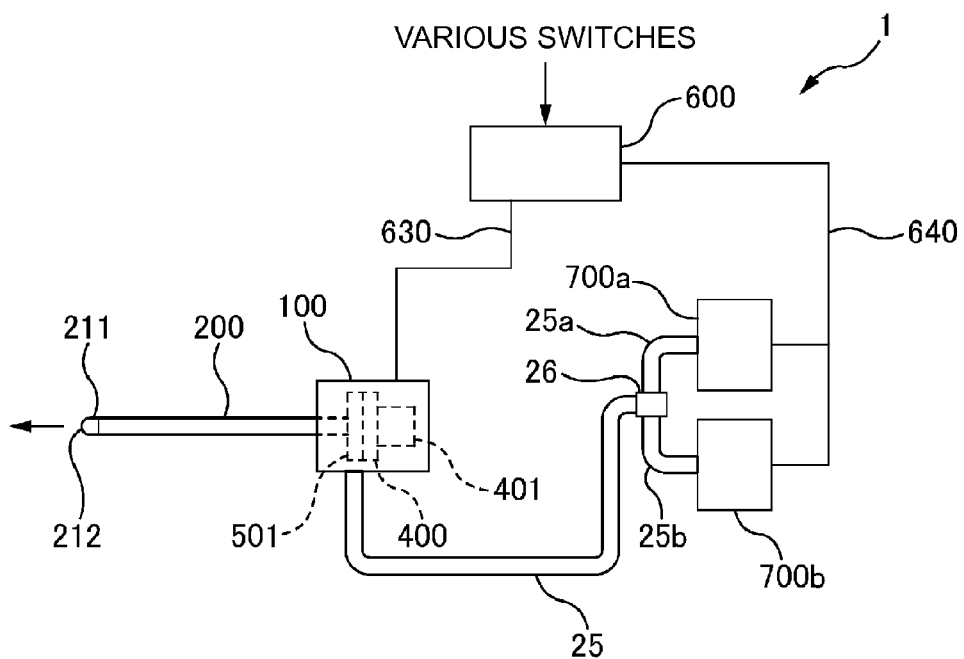
FIG. 2 is a view illustrating the configuration of the fluid ejection device configured to include two pumps.

FIG. 2 is a view illustrating the configuration of the fluid ejection device 1 configured to include two pumps 700. In this case, the fluid ejection device 1 includes a first pump 700a and a second pump 700b. A first connection tube 25a, a second connection tube 25b, the connection tube 25, and a three way stopcock 26 form a connection path which connects the pulsation generator 100 and the first pump 700a and the pulsation generator 100 and the second pump 700b, and through which the fluid flows.

The three way stopcock 26 is a valve configured to be able to communicate the first connection tube 25a and the connection tube 25, or the second connection tube 25b and the connection tube 25, and either one of the first pump 700a and the second pump 700b is selectively used.

In this configuration, for example, when the first pump 700a cannot supply the fluid for unknown reasons such as a malfunction while being selected and used, it is possible to continuously use the fluid ejection device 1 and to minimize adverse effects associated with the non-supply of the fluid from the first pump 700a by switching the three way stopcock 26 so as to communicate the second connection tube 25b and the connection tube 25, and starting the supply of the fluid from the second pump 700b.

When the fluid ejection device 1 is configured to include a plurality of the pumps 700, but the pumps 700 are not required to be distinctively described, in the following description, the pumps 700 are collectively expressed by the pump 700.

In contrast, when the plurality of pumps 700 are required to be distinctively described, suffixes such as "a" and "b" are properly added to reference sign 700 of the pump, and each of the pumps 700 is distinctively expressed by the first pump 700a or the second pump 700b. In this case, each configuration element of the first pump 700a is expressed by adding the suffix "a" to a reference sign of each configuration element, and each configuration element of the second pump 700b is expressed by adding the suffix "b" to a reference sign of each configuration element.

Pump

Figure 3:
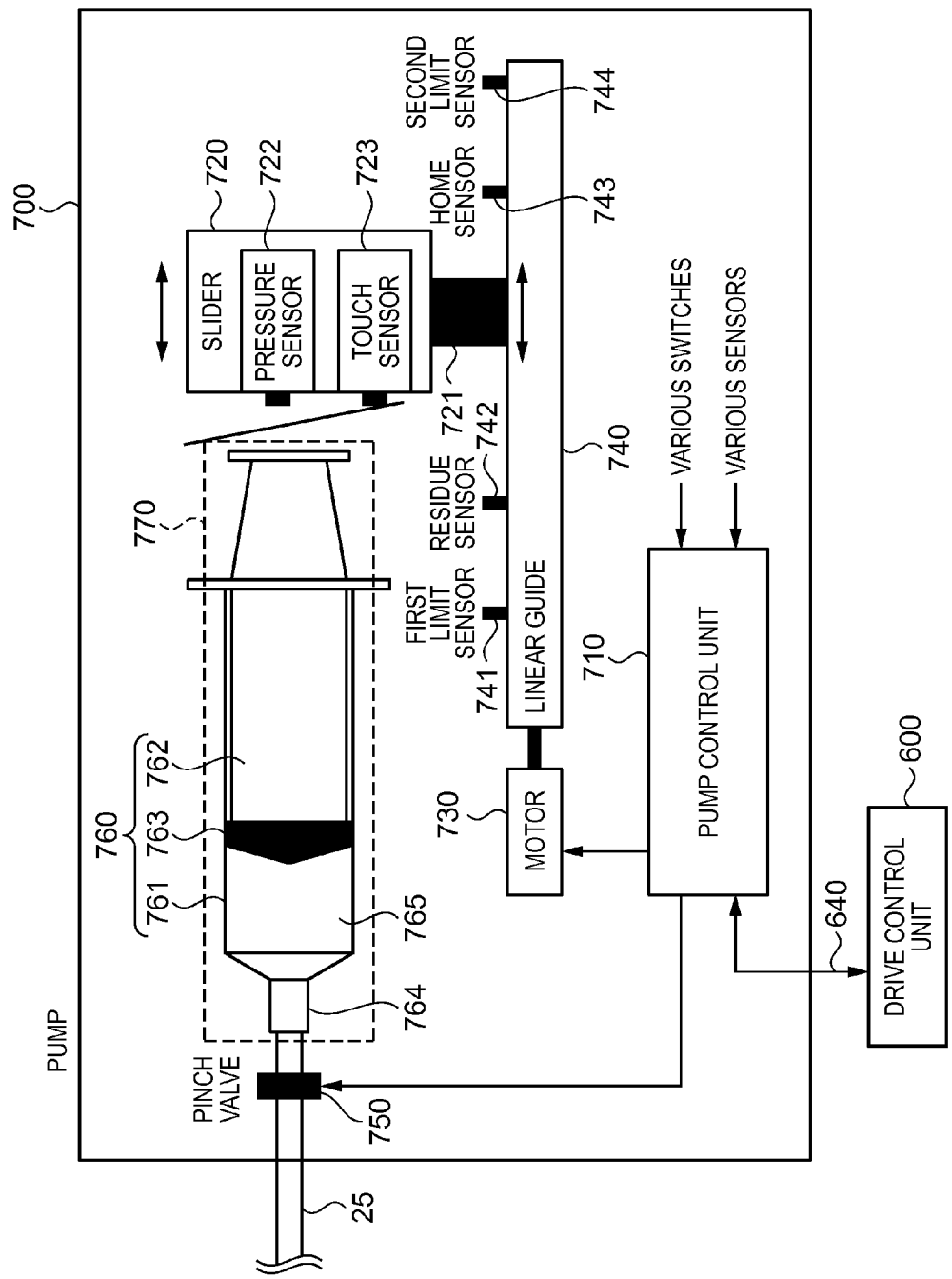
FIG. 3 is a schematic view illustrating the configuration of the pump according to the embodiment.

Subsequently, an outline of the configuration and operation of the pump 700 according to the embodiment will be described. FIG. 3 is a schematic view illustrating the configuration of the pump 700 according to the embodiment.

The pump 700 according to the embodiment includes a pump control unit (equivalent to a pressure adjustment unit) 710; a slider 720; a motor 730; a linear guide 740; and a pinch valve (equivalent to an opening and closing unit) 750. The pump 700 is configured to have a fluid container mounting unit 770 for attachably and detachably mounting a fluid container 760 that accommodates the fluid. The fluid container mounting unit 770 is formed so as to hold the fluid container 760 at a specific position when the fluid container 760 is mounted thereon.

The following switches (which will be described later in detail) (not illustrated) input signals to the pump control unit 710: a slider release switch; a slider set switch; a fluid supply ready switch; a priming switch; and a pinch valve switch.

In the embodiment, for example, the fluid container 760 is formed of a medical syringe configured to include a syringe 761 and a plunger 762.

In the fluid container 760, a protrusive cylinder-shaped opening 764 is formed in a tip end portion of the syringe 761. When the fluid container 760 is mounted on the fluid container mounting unit 770, an end portion of the connection tube 25 is inserted into the opening 764, and a fluid channel is formed from the inside of the syringe 761 to the connection tube 25.

The pinch valve 750 is a valve that is provided on a path of the connection tube 25, and opens and closes a fluid channel between the fluid container 760 and the pulsation generator 100.

The pump control unit 710 controls the opening and closing of the pinch valve 750. When the pump control unit 710 opens the pinch valve 750, the fluid container 760 and the pulsation generator 100 communicate with each other via the channel therebetween. When the pump control unit 710 closes the pinch valve 750, the channel between the fluid container 760 and the pulsation generator 100 is shut off.

In a state where the fluid container 760 is mounted on the fluid container mounting unit 770, and the pinch valve 750 is opened, when the plunger 762 of the fluid container 760 moves in a direction (hereinafter, also referred to as a push-in direction) in which the plunger 762 is pushed into the syringe 761, the volume of a space (hereinafter, also referred to as a fluid accommodation portion 765) is reduced, the space being enveloped by an end surface of a gasket 763 made of resin such as elastic rubber and mounted at the tip of the plunger 762 in the push-in direction, and an inner wall of the syringe 761, and the fluid in the fluid accommodation portion 765 is discharged via the opening 764 of the tip end portion of the syringe 761. The connection tube 25 is filled with the fluid discharged via the opening 764, and the discharged fluid is supplied to the pulsation generator 100.

In contrast, in a state where the fluid container 760 is mounted on the fluid container mounting unit 770, and the pinch valve 750 is closed, when the plunger 762 of the fluid container 760 moves in the push-in direction, it is possible to reduce the volume of the fluid accommodation portion 765, the fluid accommodating portion 765 being enveloped by the gasket 763 mounted at the tip of the plunger 762 and the inner wall of the syringe 761, and it is possible to increase the pressure of the fluid in the fluid accommodation portion 765.

The pump control unit 710 moves the slider 720 along a direction (in the push-in direction and the opposite direction of the push-in direction) in which the plunger 762 moves in a state where the fluid container 760 is mounted on the fluid container mounting unit 770, and the plunger 762 moves in accordance with the movement of the slider 720.

Specifically, the slider 720 is attached to the linear guide 740 in such a manner that a pedestal 721 of the slider 720 engages with a rail (not illustrated) formed linearly on the linear guide 740 along the slide direction of the plunger 762. The linear guide 740 moves the pedestal 721 of the slider 720 along the rail using power transmitted from the motor 730 driven by the pump control unit 710, and thereby the slider 720 moves along the slide direction of the plunger 762.

As illustrated in FIG. 3, the following sensors are provided along the rail of the linear guide 740: a first limit sensor 741; a residue sensor 742; a home sensor 743; and a second limit sensor 744.

All of the first limit sensor 741, the residue sensor 742, the home sensor 743, and the second limit sensor 744 are sensors for detecting the position of the slider 720 that moves on the rail of the linear guide 740, and signals detected by these sensors are input to the pump control unit 710.

The home sensor 743 is a sensor used to determine an initial position (hereinafter, also referred to as a home position) of the slider 720 on the linear guide 740. The home position is a position in which the slider 720 is held when the fluid container 760 is mounted or replaced.

The residue sensor 742 is a sensor for detecting the position (hereinafter, also referred to as a residual position) of the slider 720 when the residue of the fluid in the fluid container 760 is less than or equal to a predetermined value while the slider 720 moves from the home position in the push-in direction of the plunger 762. When the slider 720 reaches the residual position in which the residue sensor 742 is provided, a predetermined alarm is output to an operator (a practitioner or an assistant). The fluid container 760 currently in use is replaced with a new fluid container 760 at an appropriate time determined by the operator. Alternatively, when the second pump 700b having the same configuration as that of the pump 700 (the first pump 700a) is prepared, a switching operation is performed so as to supply the fluid from an auxiliary second pump 700b to the pulsation generator 100.

The first limit sensor 741 indicates a limit position (hereinafter, referred to as a first limit position) in a movable range in which the slider 720 can move from the home position in the push-in direction of the plunger 762. When the slider 720 reaches the first limit position in which the first limit sensor 741 is provided, the residue of the fluid in the fluid container 760 is much less than the residue indicating that the slider 720 is present at the residual position, and a predetermined alarm is output to the operator. In this case, the fluid container 760 currently in use is also replaced with a new fluid container 760, or a switching operation is also performed so as to supply the fluid from an auxiliary second pump 700b.

In contrast, the second limit sensor 744 indicates a limit position (hereinafter, also referred to as a second limit position) in a movable range in which the slider 720 can move from the home position in the opposite direction of the push-in direction of the plunger 762. When the slider 720 reaches the second limit position in which the second limit sensor 744 is provided, a predetermined alarm is output.

A touch sensor 723 and a pressure sensor 722 are mounted on the slider 720.

The touch sensor 723 is a sensor for detecting whether the slider 720 is in contact with the plunger 762 of the fluid container 760.

The pressure sensor 722 is a sensor that detects the pressure of the fluid in the fluid accommodation portion 765 formed by the inner wall of the syringe 761 and the gasket 763, and outputs signals in response to a detected pressure.

When the pinch valve 750 is closed, and the slider 720 moves in the push-in direction, and after the slider 720 comes into contact with the plunger 762, the pressure of the fluid in the fluid accommodation portion 765 increases to the extent that the slider 720 moves further in the push-in direction.

In contrast, when the pinch valve 750 is opened, and the slider 720 moves in the push-in direction, and even after the slider 720 comes into contact with the plunger 762, the fluid in the fluid accommodation portion 765 flows out of the nozzle 211 of the pulsation generator 100 via the connection tube 25, and thereby the pressure of the fluid in the fluid accommodation portion 765 increases to a certain level, but the pressure of the fluid does not increase even though the slider 720 moves further in the push-in direction.

The touch sensor 723 and the pressure sensor 722 input signals to the pump control unit 710.

A description to be given hereinafter is regarding a preparation operation configured to include a process of mounting a fluid container 760 filled with the fluid on the fluid container mounting unit 770; a process of supplying the fluid in the fluid container 760 to the pulsation generator 100; and a process of bringing the fluid ejection device 1 into a state in which the pulsation generator 100 can eject the fluid in the form of a pulsed flow.

First, the operator inputs an ON signal of the slider release switch to the pump control unit 710 by operating the slider release switch (not illustrated). Thus, the pump control unit 710 moves the slider 720 to the home position.

The operator mounts the fluid container 760 connected to the connection tube 25 in advance on the fluid container mounting unit 770. The syringe 761 of the fluid container 760 is already filled with the fluid.

When the operator sets the connection tube 25 to the pinch valve 750, and then inputs an ON signal of the pinch valve switch (not illustrated) to the pump control unit 710 by operating the pinch valve switch, the pump control unit 710 closes the pinch valve 750.

Subsequently, the operator inputs an ON signal of the slider set switch (not illustrated) to the pump control unit 710 by operating the slider set switch. Thus, the pump control unit 710 starts a control operation in such a manner that the slider 720 moves in the push-in direction and the pressure of the fluid accommodated in the fluid accommodation portion 765 of the fluid container 760 reaches a predetermined target pressure value.

Thereafter, when the operator inputs an ON signal of the fluid supply ready switch (not illustrated) to the pump control unit 710 by pushing the fluid supply switch (not illustrated), and the pressure of the fluid in the fluid container 765 enters a specific range (hereinafter, also referred to as a rough window) for the target pressure value, the pump control unit 710 is brought into a fluid suppliable state in which the fluid is allowed to be supplied from the pump 700 to the pulsation generator 100.

When the pump control unit 710 is in a fluid suppliable state, and the operator inputs an ON signal of the priming switch to the pump control unit 710 by operating the priming switch, the pump control unit 710 starts a priming process. The priming process is a process by which a fluid channel from the fluid container 760 to the connection tube 25 and to a fluid ejection opening 212 of the pulsation generator 100 is filled up with the fluid.

When the priming process starts, the pump control unit 710 opens the pinch valve 750, and starts moving the slider 720 in the push-in direction at the same time or substantially the same time (for example, a time gap of approximately several milliseconds or approximately several tens of milliseconds) as when the pinch valve 750 is opened. The slider 720 moves at a predetermined speed in such a manner that a constant amount of the fluid per unit time is supplied from the fluid container 760. The priming process is performed until a predetermined amount of time required to complete the priming process has elapsed (or the slider 720 moves by a predetermined distance), or until the operator inputs an OFF signal of the priming switch (not illustrated) by operating the priming switch.

Accordingly, a predetermined amount of the fluid in the fluid container 765 is supplied at a predetermined flow speed (the amount of discharge of the fluid per unit time) from the pump 700, the connection tube 25 from the pinch valve 750 to the pulsation generator 100 is filled up with the fluid, and the fluid chamber 501 of the pulsation generator 100, the fluid ejection tube 200 and the like are filled up with the fluid. Air present in the connection tube 25 or the pulsation generator 100 prior to the start of the priming process is released to the atmosphere via the nozzle 211 of the pulsation generator 100 as the fluid flows into the connection tube 25 or the pulsation generator 100.

The pump control unit 710 pre-stores the predetermined speed, the predetermined distance, and the predetermined amount of time in relation to the movement of the slider 720 during the priming process.

As such, the priming process is completed.

Subsequently, when the operator inputs an ON signal of the flushing switch (not illustrated) to the drive control unit 600 by operating the flushing switch, the drive control unit 600 and the pump control unit 710 start a deaeration process.

The deaeration process is a process by which air bubbles remaining in the connection tube 25 or the pulsation generator 100 are discharged via the nozzle 211 of the pulsation generator 100.

In the deaeration process, in a state in which the pinch valve 750 is opened, the pump control unit 710 moves the slider 720 in the push-in direction at the predetermined speed in such a manner that a constant amount of the fluid per unit time is supplied from the fluid container 760, and the fluid is supplied to the pulsation generator 100. The drive control unit 600 drives the piezoelectric element 401 of the pulsation generator 100 in conjunction with the discharge of the fluid by the pump 700, and thereby the pulsation generator 100 ejects the fluid. Accordingly, air bubbles remaining in the connection tube 25 or the pulsation generator 100 are discharged via the nozzle 211 of the pulsation generator 100. The deaeration process is performed until a predetermined amount of time has elapsed (or the slider 720 moves by a predetermined distance), or until the operator inputs an OFF signal of the flushing switch (not illustrated) by operating the flushing switch.

The drive control unit 600 and the pump control unit 710 pre-store the predetermined speed, the predetermined distance, and the predetermined amount of time in relation to the movement of the slider 720 during the deaeriation process.

When the deaeriation process is completed, the pump control unit 710 closes the pinch valve 750, and detects the pressure of the fluid accommodated in the fluid accommodation portion 765 of the fluid container 760. The pump control unit 710 performs a control operation of adjusting the position of the slider 720 in such a manner that the pressure reaches the target pressure value.

Thereafter, when the pressure of the fluid in the fluid container 765 enters a specific range (a rough window) for the target pressure value, the pump control unit 710 is brought into a fluid ejectable state in which the fluid can be ejected in the form of a pulsed flow from the pulsation generator 100.

In this state, when the operator inputs an ON signal of the pulsation generator start-up switch (not illustrated) to the drive control unit 600 by operating the pulsation generator start-up switch via the feet, the pump control unit 710 opens the pinch valve 750 in response to signals transmitted from the drive control unit 600, and starts the supply of the fluid to the pulsation generator 100 by moving the slider 720 at a predetermined speed in the push-in direction at the same time or substantially the same time (for example, a time gap of approximately several milliseconds or approximately several tens of milliseconds) as when the pinch valve 750 is opened. In contrast, the drive control unit 600 generates a pulsed flow by starting the driving of the piezoelectric element 401 and changing the volume of the fluid chamber 501. Accordingly, a pulsed flow of the fluid is ejected at a high speed via the nozzle 211 at the tip of the pulsation generator 100.

Thereafter, when the operator inputs an OFF signal of the pulsation generator start-up switch (not illustrated) to the drive control unit 600 by operating the pulsation generator start-up switch via the feet, the drive control unit 600 stops the driving of the piezoelectric element 401. The pump control unit 710 stops the movement of the slider 720 in response to signals transmitted from the drive control unit 600, and closes the pinch valve 750. As such, the pulsation generator 100 stops the ejection of the fluid.

Figure 4:
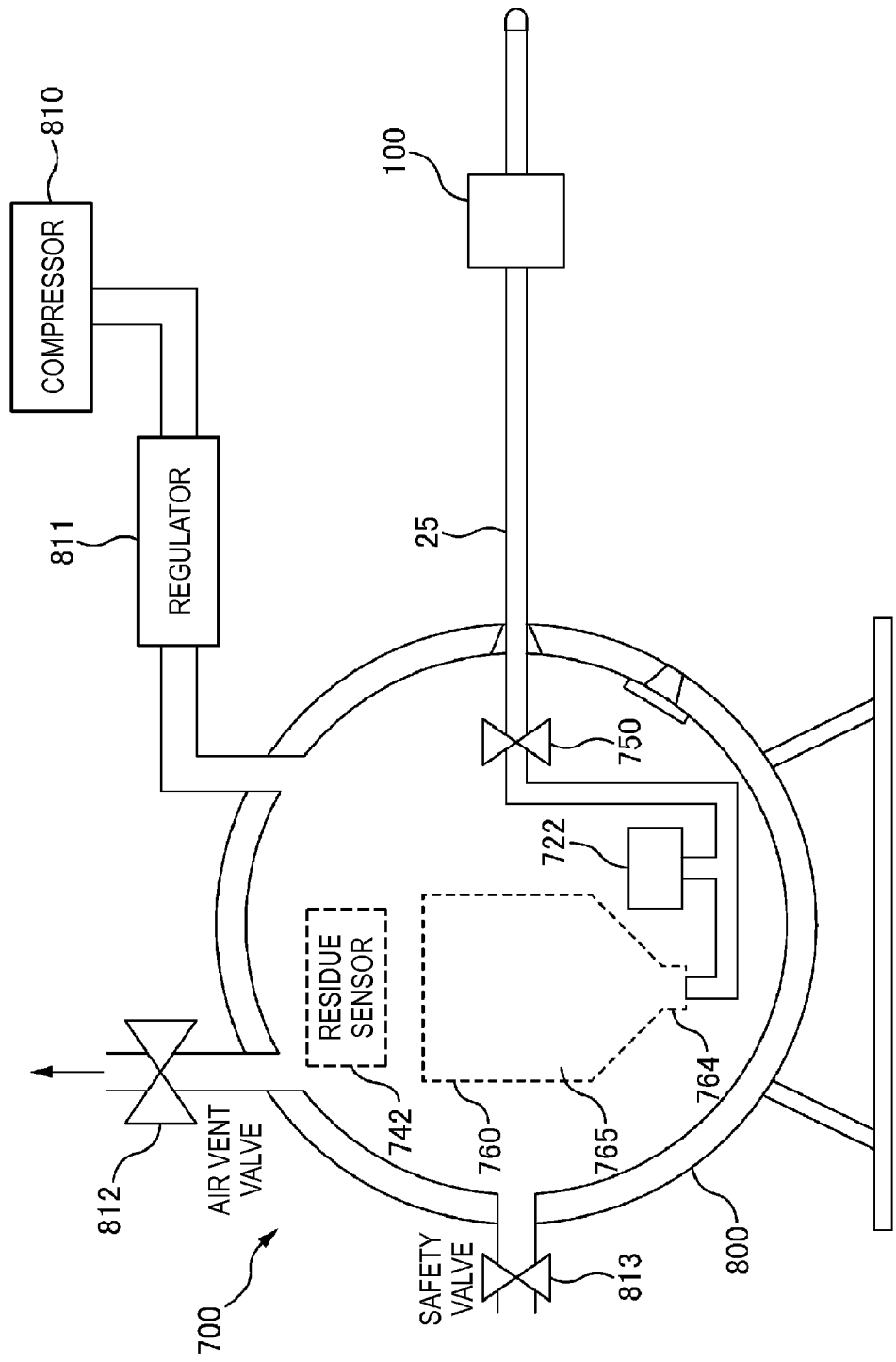
FIG. 4 is a view illustrating the pump with a different configuration.

The pump 700 according to the embodiment is configured such that the slider 720 presses the fluid container 760 that is formed of a medical syringe configured to include the syringe 761 and the plunger 762; however, the pump 700 may be configured as illustrated in FIG. 4.

FIG. 4 is a view illustrating the pump 700 with a different configuration. The pump 700 illustrated in FIG. 4 has the following configuration: the fluid container 760 (an infusion solution bag that accommodates a fluid) is mounted in a pressurized chamber 800, and after air supplied from a compressor 810 is regulated by a regulator 811, the air is pressure-fed into the pressurized chamber 800, and thereby the fluid container 760 is pressed.

When the pinch valve 750 is opened in a state where the fluid container 760 is pressed by the pressurization of air in the pressurized chamber 800, the fluid accommodated in the fluid accommodation portion 765 of the fluid container 760 flows out of the opening 764, and is supplied to the pulsation generator 100 via the connection tube 25.

The air in the pressurized chamber 800 is released to the atmosphere by the opening of an air vent valve 812. In a case where the pressure of the air in the pressurized chamber 800 exceeds a predetermined pressure, even when the air vent valve 812 is not opened, a safety valve 813 is opened, and thereby the air in the pressurized chamber 800 is released to the atmosphere.

The pump control unit 710 controls the compressor 810; the regulator 811; the air vent valve 812; and the pinch valve 750, the control scheme of which is not illustrated in FIG. 4. The following sensors input detected output signals to the pump control unit 710: the pressure sensor 722 that detects the pressure of the fluid in the fluid container 760, and the residue sensor 742 that detects the residue of the fluid in the fluid container 760.

When the pump 700 with this configuration is adopted, it is possible to increase the amount of supply of the fluid which can be supplied to the pulsation generator 100 per unit time. Since the pulsation generator 100 can supply the fluid at a high pressure, and an infusion solution bag that accommodates the fluid is used as the fluid container 760 as it is, it is possible to prevent the fluid from being contaminated. The pulsation generator 100 can continuously supply the fluid without generating pulsation.

In addition, in the embodiment, the drive control unit 600 is provided separately from the pump 700 and the pulsation generator 100; however, the drive control unit 600 may be provided integrally with the pump 700.

When the practitioner performs an operation using the fluid ejection device 1, the practitioner grasps the pulsation generator 100. Accordingly, the connection tube 25 up to the pulsation generator 100 is preferably as flexible as possible. For this reason, a flexible thin tube is used as the connection tube 25, and a fluid discharge pressure of the pump 700 is preferably set to a low pressure in a pressure range in which the fluid can be supplied to the pulsation generator 100. For this reason, the discharge pressure of the pump 700 is set to approximately 0.3 atm (0.03 MPa) or less.

In particular, in a case where a malfunction of an apparatus may lead to a serious accident, for example, for brain surgery, it is necessary to prevent the cutting of the connection tube 25 from causing the ejection of the fluid at a high pressure, and also, for this reason, the discharge pressure of the pump 700 is required to be set to a low pressure.

Pulsation Generator

Subsequently, the structure of the pulsation generator 100 according to the embodiment will be described.

Figure 5:
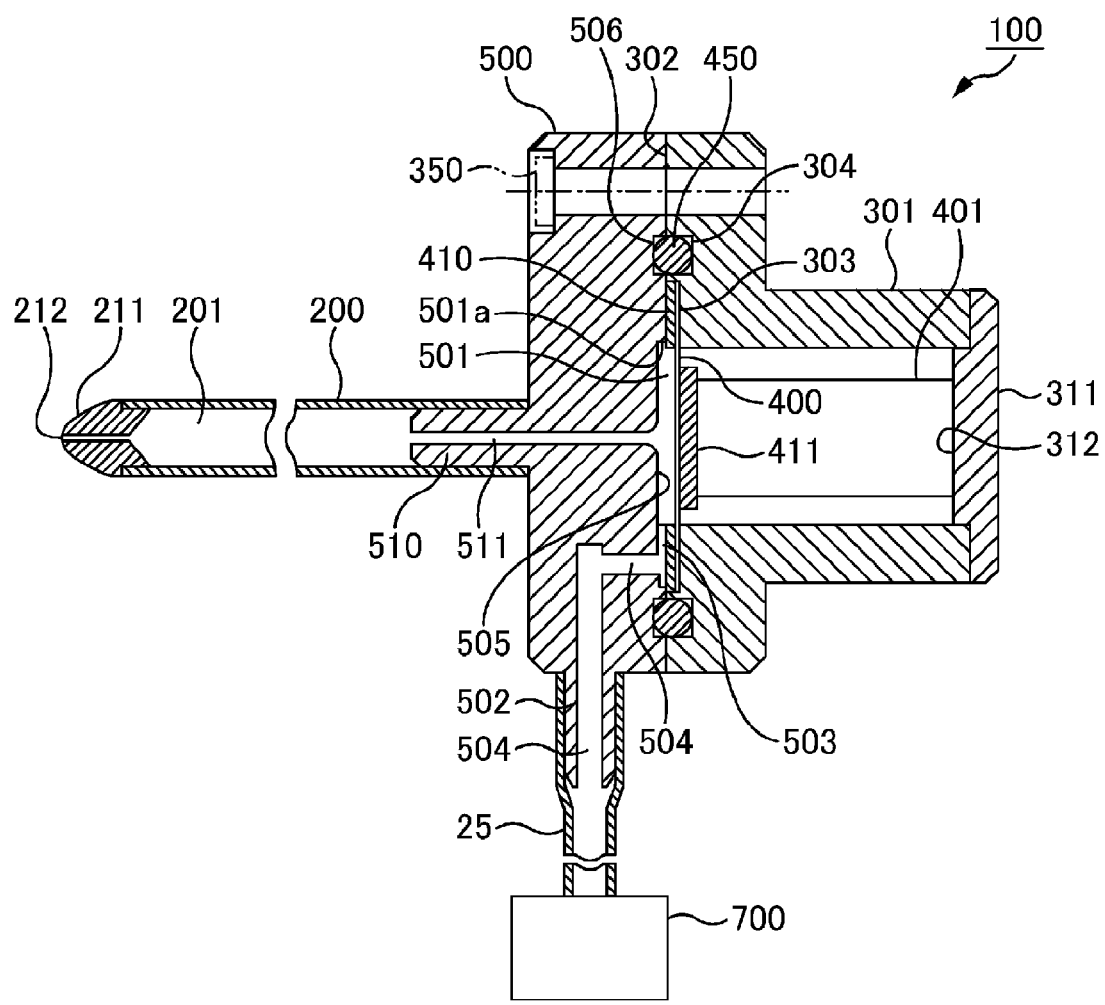
FIG. 5 is a cross-sectional view illustrating the structure of a pulsation generator according to the embodiment.

FIG. 5 is a cross-sectional view illustrating the structure of the pulsation generator 100 according to the embodiment. In FIG. 5, the pulsation generator 100 includes a pulse generation unit that generates the pulsation of the fluid, and is connected to the fluid ejection tube 200 having a connection channel 201 as a channel through which the fluid is discharged.

In the pulsation generator 100, an upper case 500 and a lower case 301 are screwed together with four fixation screws 350 (not illustrated) while the respective facing surfaces thereof are bonded to each other. The lower case 301 is a cylindrical member having a flange, and one end portion of the lower case 301 is sealed with a bottom plate 311. The piezoelectric element 401 is provided in an inner space of the lower case 301.

The piezoelectric element 401 is a stack-type piezoelectric element, and acts as an actuator. One end portion of the piezoelectric element 401 is firmly fixed to the diaphragm 400 via an upper plate 411, and the other end portion is firmly fixed to an upper surface 312 of the bottom plate 311.

The diaphragm 400 is made of a circular disc-like thin metal plate, and a circumferential edge portion of the diaphragm 400 is firmly fixed to a bottom surface of a concave portion 303 in the lower case 301 while being in close contact with the bottom surface of the concave portion 303. When drive signals are input to the piezoelectric element 401 that acts as a volume change unit, the piezoelectric element 401 changes the volume of the fluid chamber 501 via the diaphragm 400 through the extension and contraction thereof.

A reinforcement plate 410 is provided in such a manner as to be stacked on an upper surface of the diaphragm 400, and is made of a circular disc-like thin metal plate having an opening at the center thereof.

The upper case 500 has a concave portion formed in a center portion of the surface facing the lower case 301, and the fluid chamber 501 is a rotator-shaped space formed by this concave portion and the diaphragm 400 and filled with the fluid. That is, the fluid chamber 501 is a space enveloped by a sealing surface 505 and an inner circumferential side wall 501a of the concave portion of the upper case 500, and the diaphragm 400. An outlet channel 511 is drilled in an approximately center portion of the fluid chamber 501.

The outlet channel 511 passes through the outlet channel tube 510 from the fluid chamber 501 to an end portion of an outlet channel tube 510 provided in such a manner as to protrude from one end surface of the upper case 500. A connection portion between the outlet channel 511 and the sealing surface 505 of the fluid chamber 501 is smoothly rounded so as to reduce fluid resistance.

In the embodiment (refer to FIG. 5), the fluid chamber 501 has a substantially cylindrical shape having sealed opposite ends; however, the fluid chamber 501 may have a conical shape, a trapezoidal shape, a hemispherical shape, or the like in a side view, and the shape of the fluid chamber 501 is not limited to a cylindrical shape. For example, when the connection portion between the outlet channel 511 and the sealing surface 505 has a funnel shape, air bubbles in the fluid chamber 501 (to be described later) are easily discharged.

The fluid ejection tube 200 is connected to the outlet channel tube 510. The connection channel 201 is drilled in the fluid ejection tube 200, and the diameter of the connection channel 201 is larger than that of the outlet channel 511. In addition, the tube thickness of the fluid ejection tube 200 is formed so as to have a range of rigidity in which the fluid ejection tube 200 does not absorb pressure pulsation of the fluid.

The nozzle 211 is inserted into the tip end portion of the fluid ejection tube 200. A fluid ejection opening 212 is drilled in the nozzle 211. The diameter of the fluid ejection opening 212 is smaller than that of the connection channel 201.

An inlet channel tube 502 is provided in such a manner as to protrude from a side surface of the upper case 500, and is inserted into the connection tube 25 through which the fluid is supplied from the pump 700. A connection channel 504 for the inlet channel is drilled in the inlet channel tube 502. The connection channel 504 communicates with an inlet channel 503. The inlet channel 503 is formed in a groove shape in a circumferential edge portion of the sealing surface 505 of the fluid chamber 501, and communicates with the fluid chamber 501.

A packing box 304 and a packing box 506 are respectively formed in the bonded surfaces of the lower case 301 and the upper case 500 at positions separated from an outer circumferential direction of the diaphragm 400, and a ring-shaped packing 450 is mounted in a space formed by the packing boxes 304 and 506.

Here, when the upper case 500 and the lower case 301 are assembled together, the circumferential edge portion of the diaphragm 400 is in close contact with a circumferential edge portion of the reinforcement plate 410 due to the circumferential edge portion of the sealing surface 505 of the upper case 500 and the bottom surface of the concave portion 303 of the lower case 301. At this time, the packing 450 is pressed by the upper case 500 and the lower case 301, and thereby the fluid is prevented from leaking from the fluid chamber 501.

Since the inner pressure of the fluid chamber 501 becomes a high pressure of 30 atm (3 MPa) or greater during the discharge of the fluid, the fluid may slightly leak from the respective connections between the diaphragm 400, the reinforcement plate 410, the upper case 500, and the lower case 301; however, the leakage of the fluid is prevented due to the packing 450.

As illustrated in FIG. 5, in the case where the packing 450 is provided, since the packing 450 is compressed due to the pressure of the fluid leaking from the fluid chamber 501 at a high pressure, and is strongly pressed against the respective walls of the packing boxes 304 and 506, it is possible to more reliably prevent the leakage of the fluid. For this reason, it is possible to maintain a considerable increase in the inner pressure of the fluid chamber 501 during the driving of the pulsation generator 100.

Subsequently, the inlet channel 503 formed in the upper case 500 will be described with reference to the drawings in more detail.

Figure 6:
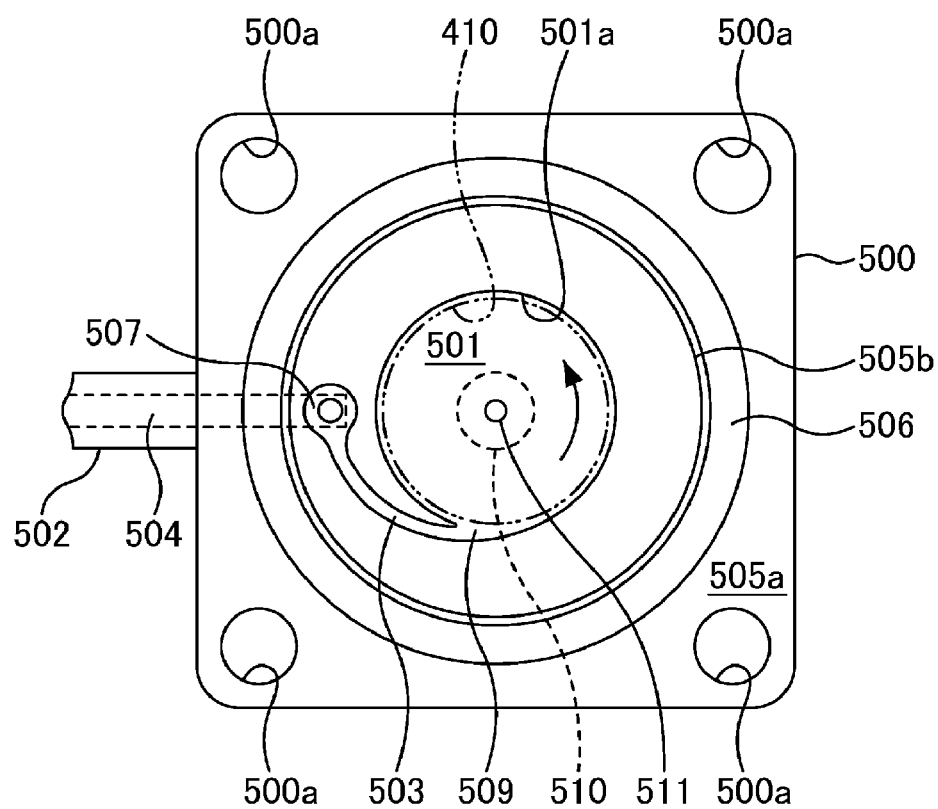
FIG. 6 is a plan view illustrating the shape of an inlet channel.

FIG. 6 is a plan view illustrating the shape of the inlet channel 503. FIG. 6 illustrates the shape of the upper case 500 when the surface of the upper case 500 bonded to the lower case 301 is seen.

In FIG. 6, the inlet channel 503 is formed in a groove shape in the circumferential edge portion of the sealing surface 505 of the upper case 500.

One end portion of the inlet channel 503 communicates with the fluid chamber 501, and the other end portion communicates with the connection channel 504. A fluid sump 507 is formed in a connection portion between the inlet channel 503 and the connection channel 504. A connection portion between the fluid sump 507 and the inlet channel 503 is smoothly rounded, and thereby fluid resistance is reduced.

The inlet channel 503 communicates with the fluid chamber 501 in a substantially tangential direction with respect to an inner circumferential side wall 501a of the fluid chamber 501. The fluid supplied from the pump 700 (refer to FIG. 1) at a predetermined pressure flows along the inner circumferential side wall 501a (in a direction illustrated by the arrow in FIG. 6), and generates a swirl flow in the fluid chamber 501. The swirl flow is pushed against the inner circumferential side wall 501a due to a centrifugal force associated with the swirling of the fluid, and air bubbles in the fluid chamber 501 are concentrated in a center portion of the swirl flow.

The air bubbles concentrated in the center portion are discharged via the outlet channel 511. For this reason, the outlet channel 511 is preferably provided in the vicinity of the center of the swirl flow, that is, in an axial center portion of a rotor shape.

As illustrated in FIG. 6, the inlet channel 503 is curved. The inlet channel 503 may communicate with the fluid chamber 501 while not being curved but being linearly formed; however, when the inlet channel 503 is curved, a channel length is increased, and a desired inertance (to be described later) is obtained in a small space.

As illustrated in FIG. 6, the reinforcement plate 410 is provided between the diaphragm 400 and the circumferential edge portion of the sealing surface 505, in which the inlet channel 503 is formed. The reinforcement plate 410 is provided so as to improve the durability of the diaphragm 400. Since a cut-out connection opening 509 is formed in a connection portion between the inlet channel 503 and the fluid chamber 501, when the diaphragm 400 is driven at a high frequency, stress may be concentrated in the vicinity of the connection opening 509, and thereby a fatigue failure may occur in the vicinity of the connection opening 509. It is possible to prevent stress from being concentrated on the diaphragm. 400 by providing the reinforcement plate 410 with an opening not having a cut-out portion and being continuously formed.

Four screw holes 500a are respectively provided in outer circumferential corner portions of the upper case 500, and the upper case 500 and the lower case 301 are bonded to each other via screwing at the positions of the screw holes.

It is possible to firmly fix the reinforcement plate 410 and the diaphragm 400 in an integrally stacked state by bonding together the reinforcement plate 410 and the diaphragm 400, which is not illustrated. An adhesive method using an adhesive, a solid-state diffusion bonding method, a welding method, or the like may be used so as to firmly fix together the reinforcement plate 410 and the diaphragm 400; however, the respective bonded surfaces of the reinforcement plate 410 and the diaphragm 400 are preferably in close contact with each other.

Operation of Pulsation Generator

Subsequently, an operation of the pulsation generator 100 according to the embodiment will be described with reference to FIGS. 1 to 6. The pulsation generator 100 according to the embodiment discharges the fluid due to a difference between an inertance L1 (may be referred to as a combined inertance L1) of the inlet channel 503 and the peripherals and an inertance L2 (may be referred to as a combined inertance L2) of the outlet channel 511 and the peripherals.

Inertance

First, the inertance will be described.

An inertance L is expressed by $L=\rho \times h/S$, and here, $\rho$ is the density of a fluid, S is the cross-sectional area of a channel, and h is a channel length. When $\Delta P$ is a differential pressure of the channel, and Q is a flow rate of the fluid flowing through the channel, it is possible to deduce a relationship $\Delta P = L \times dQ/dt$ by modifying an equation of motion in the channel using the inertance L.

That is, the inertance L indicates a degree of influence on a change in flow rate with time, and a change in flow rate with time decreases to the extent that the inertance L is large, and a change in flow rate with time increases to the extent that the inertance L is small.

Similar to a parallel connection or a series connection of inductances in an electric circuit, it is possible to calculate a combined inertance with respect to a parallel connection of a plurality of channels or a series connection of a plurality of channels having different shapes by combining an inertance of each of the channels.

Since the diameter of the connection channel 504 is set to be larger much than that of the inlet channel 503, the inertance L1 of the inlet channel 503 and the peripherals can be calculated from a boundary of the inlet channel 503. At this time, since the connection tube 25 that connects the pump 700 and the inlet channel 503 is flexible, the connection tube 25 may not be taken into consideration in calculating the inertance L1.

Since the diameter of the connection channel 201 is larger much than that of the outlet channel 511, and the tube (tube wall) thickness of the fluid ejection tube 200 is thin, the connection tube 25 and the fluid ejection device 1 have a negligible influence on the inertance L2 of the outlet channel 511 and the peripherals. Accordingly, the inertance L2 of the outlet channel 511 and the peripherals may be replaced with an inertance of the outlet channel 511.

The rigidity of the tube wall thickness of the fluid ejection tube 200 is sufficient to propagate the pressure of the fluid.

In the embodiment, a channel length and a cross-sectional area of the inlet channel 503 and a channel length and a cross-sectional area of the outlet channel 511 are set in such a manner that the inertance L1 of the inlet channel 503 and the peripherals are greater than the inertance L2 of the outlet channel 511 and the peripherals.

Ejection of Fluid

Subsequently, an operation of the pulsation generator 100 will be described.

The pump 700 supplies the fluid to the inlet channel 503 at a predetermined pressure. As a result, when the piezoelectric element 401 is not operated, the fluid flows into the fluid chamber 501 due to a difference between a discharge force of the pump 700 and a fluid resistance value for the entirety of the inlet channel 503 and the peripherals.

Here, in a case where the inertance L1 of the inlet channel 503 and the peripherals and the inertance L2 of the outlet channel 511 and the peripherals are considerably large, when a drive signal is input to the piezoelectric element 401, and the piezoelectric element 401 extends rapidly, the inner pressure of the fluid chamber 501 increases rapidly, and reaches several tens of atmosphere.

Since the inner pressure of the fluid chamber 501 is larger much than the pressure applied to the inlet channel 503 by the pump 700, the flow of the fluid from the inlet channel 503 to the fluid chamber 501 decreases due to the pressure, and the flow of the fluid out of the outlet channel 511 increases.

Since the inertance L1 of the inlet channel 503 is larger than the inertance L2 of the outlet channel 511, an increase in a flow rate of the fluid discharged from the outlet channel 511 is larger than a decrease in a flow rate of the fluid flowing from the inlet channel 503 into the fluid chamber 501. Accordingly, the fluid is discharged in the form of a pulsed flow to the connection channel 201, that is, a pulsed flow occurs. Discharge pressure pulsation propagates in the fluid ejection tube 200, and the fluid is ejected via the fluid ejection opening 212 of the nozzle 211 at the tip end.

Here, since the diameter of the fluid ejection opening 212 of the nozzle 211 is smaller than that of the outlet channel 511, a pulsed flow of the fluid is ejected as droplets at a higher pressure and speed.

In contrast, immediately after a pressure increase, the inner pressure of the fluid chamber 501 becomes negative due to interaction between a decrease in the amount of inflow of the fluid from the inlet channel 503 and an increase in the amount of outflow of the fluid from the outlet channel 511. As a result, after a predetermined amount of time has elapsed, due to both of the pressure of the pump 700 and the negative inner pressure of the fluid chamber 501, the fluid flows from the inlet channel 503 into the fluid chamber 501 again at the same speed as that before the operation of the piezoelectric element 401.

When the piezoelectric element 401 extends after the flow of the fluid from the inlet channel 503 is restored, it is possible to continuously eject the fluid in the form of a pulsed flow via the nozzle 211.

Discharge of Air Bubbles

Subsequently, an operation of discharging air bubbles from the fluid chamber 501 will be described.

As described above, the inlet channel 503 communicates with the fluid chamber 501 via a path that approaches the fluid chamber 501 while swirling around the fluid chamber 501. The outlet channel 511 is provide in the vicinity of a rotational axis of a substantially rotor-shaped fluid chamber 501.

For this reason, the fluid flowing from the inlet channel 503 into the fluid chamber 501 swirls along the inner circumferential side wall 501a of the fluid chamber 501. The fluid is pushed against the inner circumferential side wall 501a of the fluid chamber 501 due to a centrifugal force, and air bubbles contained in the fluid are concentrated in the center portion of the fluid chamber 501, and are discharged via the outlet channel 511.

Accordingly, even when a small amount of the volume of the fluid chamber 501 is changed in association with the operation of the piezoelectric element 401, it is possible to obtain a sufficient pressure increase while a pressure pulsation is not adversely affected by the air bubbles.

In the embodiment, since the pump 700 supplies the fluid to the inlet channel 503 at a predetermined pressure, even when the driving of the pulsation generator 100 is stopped, the fluid is supplied to the inlet channel 503 and the fluid chamber 501. Accordingly, it is possible to start an initial operation without an aid of a prime operation.

Since the fluid is ejected via the fluid ejection opening 212 having a diameter smaller than that of the outlet channel 511, an inner fluid pressure increases higher than that of the outlet channel 511, and thereby it is possible to eject the fluid at a high speed.

Since the rigidity of the fluid ejection tube 200 is sufficient to transmit a pulsation of the fluid from the fluid chamber 501 to the fluid ejection opening 212, it is possible to eject the fluid in the form of a desired pulsed flow without disturbing pressure propagation of the fluid from the pulsation generator 100.

Since the inertance of the inlet channel 503 is set to be larger than that of the outlet channel 511, an increase in the amount of outflow of the fluid from the outlet channel 511 is larger than a decrease in the amount of inflow of the fluid from the inlet channel 503 into the fluid chamber 501, and it is possible to discharge the fluid into the fluid ejection tube 200 in the form of a pulsed flow. Accordingly, a check valve is not required to be provided in the inlet channel 503, it is possible to simplify the structure of the pulsation generator 100, it is easy to clean the inside of the pulsation generator 100, and it is possible to remove a potential durability problem associated with the use of the check valve.

Since the respective inertances of both of the inlet channel 503 and the outlet channel 511 are set to be considerably large, it is possible to rapidly increase the inner pressure of the fluid chamber 501 by rapidly reducing the volume of the fluid chamber 501.

Since the piezoelectric element 401 as a volume change unit and the diaphragm 400 are configured so as to generate a pulsation, it is possible to simplify the structure of the pulsation generator 100 and to reduce the size of the pulsation generator 100 in association therewith. It is possible to set the maximum frequency of a change in the volume of the fluid chamber 501 to a high frequency of 1 KHz or greater, and the pulsation generator 100 is optimized to eject a pulsed flow of the fluid at a high speed.

In the pulsation generator 100, since the inlet channel 503 generates a swirl flow of the fluid in the fluid chamber 501, the fluid in the fluid chamber 501 is pushed in an outer circumferential direction of the fluid chamber 501 due to a centrifugal force, air bubbles contained in the fluid are concentrated in the center portion of the swirl flow, that is, in the vicinity of the axis of the substantially rotor shape, and thereby it is possible to discharge the air bubbles via the outlet channel 511 provided in the vicinity of the axis of the substantially rotor shape. For this reason, it is possible to prevent a decrease in pressure amplitude associated with the stagnation of air bubbles in the fluid chamber 501, and it is possible to continuously and stably drive the pulsation generator 100.

Since the inlet channel 503 is formed in such a manner as to communicate with the fluid chamber 501 via the path that approaches the fluid chamber 501 while swirling around the fluid chamber 501, it is possible to generate a swirl flow without adopting a structure dedicated for swirling the fluid in the fluid chamber 501.

Since the groove-shaped inlet channel 503 is formed in the outer circumferential edge portion of the sealing surface 505 of the fluid chamber 501, it is possible to form the inlet channel 503 (a swirl flow generation unit) without increasing the number of components.

Since the reinforcement plate 410 is provided on the upper surface of the diaphragm 400, the diaphragm 400 is driven with respect to an outer circumference (a fulcrum) of the opening of the reinforcement plate 410, and thereby the concentration of stress is unlikely to occur, and it is possible to improve the durability of the diaphragm 400.

When corners of the surface of the reinforcement plate 410 bonded to the diaphragm 400 are rounded, it is possible to further reduce the concentration of stress on the diaphragm 400.

When the reinforcement plate 410 and the diaphragm 400 are firmly and integrally fixed together while being stacked on each other, it is possible to improve the assemblability of the pulsation generator 100, and it is possible to reinforce the outer circumferential edge portion of the diaphragm 400.

Since the fluid sump 507 for the stagnation of the fluid is provided in the connection portion between the connection channel 504 on an inlet side for supplying the fluid from the pump 700 and the inlet channel 503, it is possible to prevent the inertance of the connection channel 504 from affecting the inlet channel 503.

In the respective bonded surfaces of the lower case 301 and the upper case 500, the ring-shaped packing 450 is provided at the position separated from the outer circumferential direction of the diaphragm 400, and thereby it is possible to prevent the leakage of the fluid from the fluid chamber 501, and to prevent a decrease in the inner pressure of the fluid chamber 501.

Control of Inner Pressure of Fluid Container 760

Figure 7:
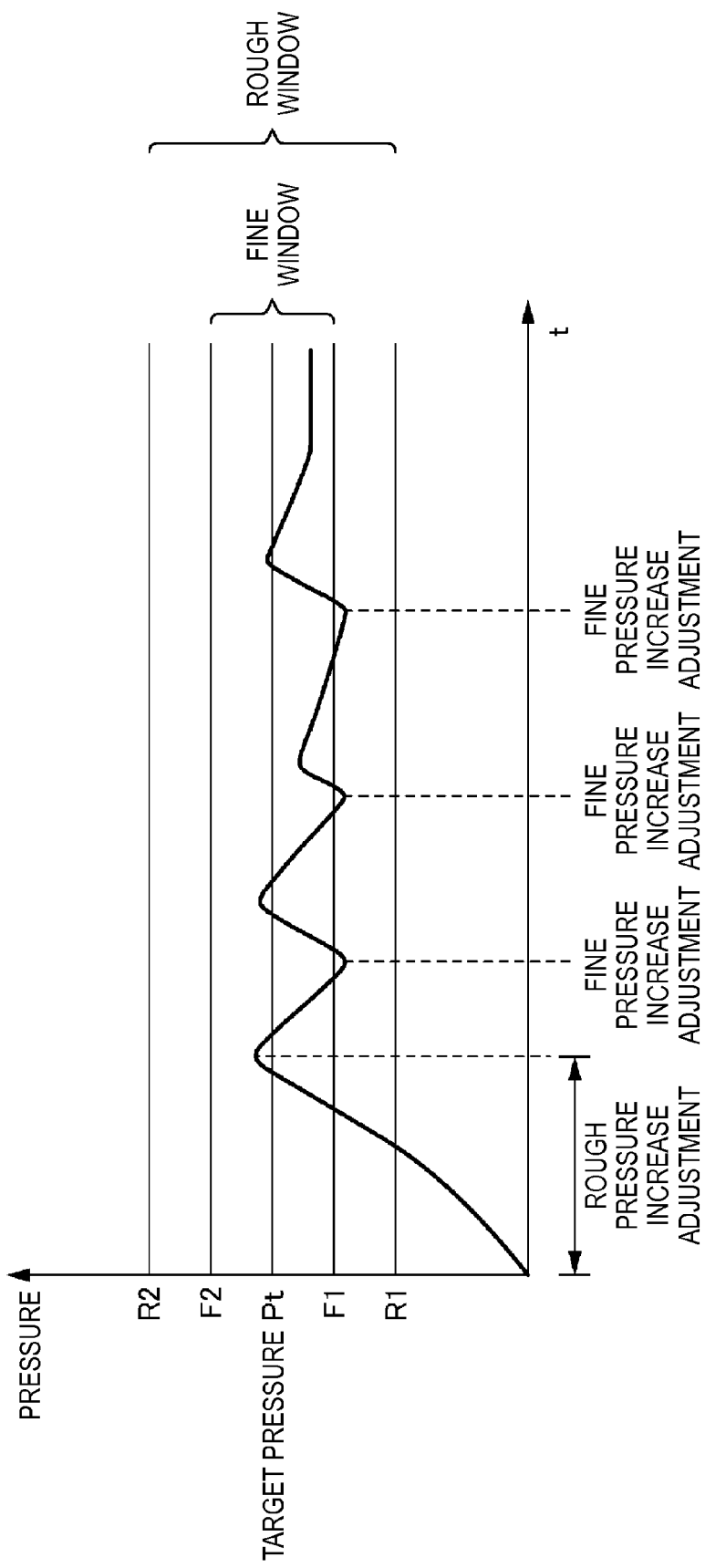
FIG. 7 is a graph illustrating a transition of an inner pressure of a fluid container when a pressure control operation is performed.

FIG. 7 is a graph illustrating a transition of the inner pressure of the fluid container 760 when a pressure control operation is performed. FIG. 7 illustrates a pressure P (on a vertical axis) with respect to a time t (on a horizontal axis). The pressure P illustrated here indicates the inner pressure of the fluid container 760 (hereinafter, the inner pressure of the fluid chamber 760 may be simply referred to as the "pressure P"), which is detected by the pressure sensor 722. FIG. 7 illustrates a target pressure Pt, a pressure R1, a pressure F1 higher than the pressure R1, a pressure F2 higher than the pressure F1 and the target pressure, and a pressure R2 higher than the pressure F2. A rough window indicates a range from the pressure R1 to the pressure R2. A fine window indicates a range from the pressure F1 to the pressure F2.

An outline of the fluid ejection device 1 according to the embodiment will be described. The drive control unit 600 of the fluid ejection device 1 controls the ejection of the fluid from the pulsation generator 100. The pump control unit 710 of the fluid ejection device 1 controls the inner pressure of the fluid container 760.

When the inner pressure P of the fluid container 760 is higher than the pressure R1 and is lower than the pressure R2, the drive control unit 600 receives a demand for the ejection of the fluid from the pulsation generator start-up switch (not illustrated), and controls the pulsation generator 100 to eject the fluid. That is, when the pressure P is in the rough window, the fluid is ejected. Even in the case where the pressure P is higher than the pressure R1 and is lower than the pressure R2, when the fluid ejection device 1 is in a trial mode (equivalent to a second ejection mode) (to be described later), the fluid is ejected, which is an exceptional case. At this time, the pump control unit 710 does not control the pressure of the fluid container 760, and sends a constant amount of the fluid from the fluid container 760 to the pulsation generator 100.

In a pressure adjustment control operation (to be described later), the pump control unit 710 performs a rough pressure increase adjustment control operation when the pressure P is the pressure R1 or lower. When the pressure P is higher than the pressure R1, and is the pressure F1 or lower, the pump control unit 710 performs a fine pressure increase adjustment control operation. When the pressure P is higher than the pressure F1 and is lower than the pressure F2 (in the fine window), the pump control unit 710 does not perform a pressure adjustment operation. When the pressure P is the pressure F2 or higher, the pump control unit 710 performs a fine pressure decrease adjustment control operation. When the pump control unit 710 performs the pressure adjustment control operation, the drive control unit 600 controls the pulsation generator 100 not to eject the fluid.

Hereinafter, the pressure adjustment control operation will be described. In the following description, the inner pressure P of the fluid container 760 is detected by the pressure sensor 722, and the pump control unit 710 performs the pressure adjustment control operation in response to the pressure P.

Figure 8:
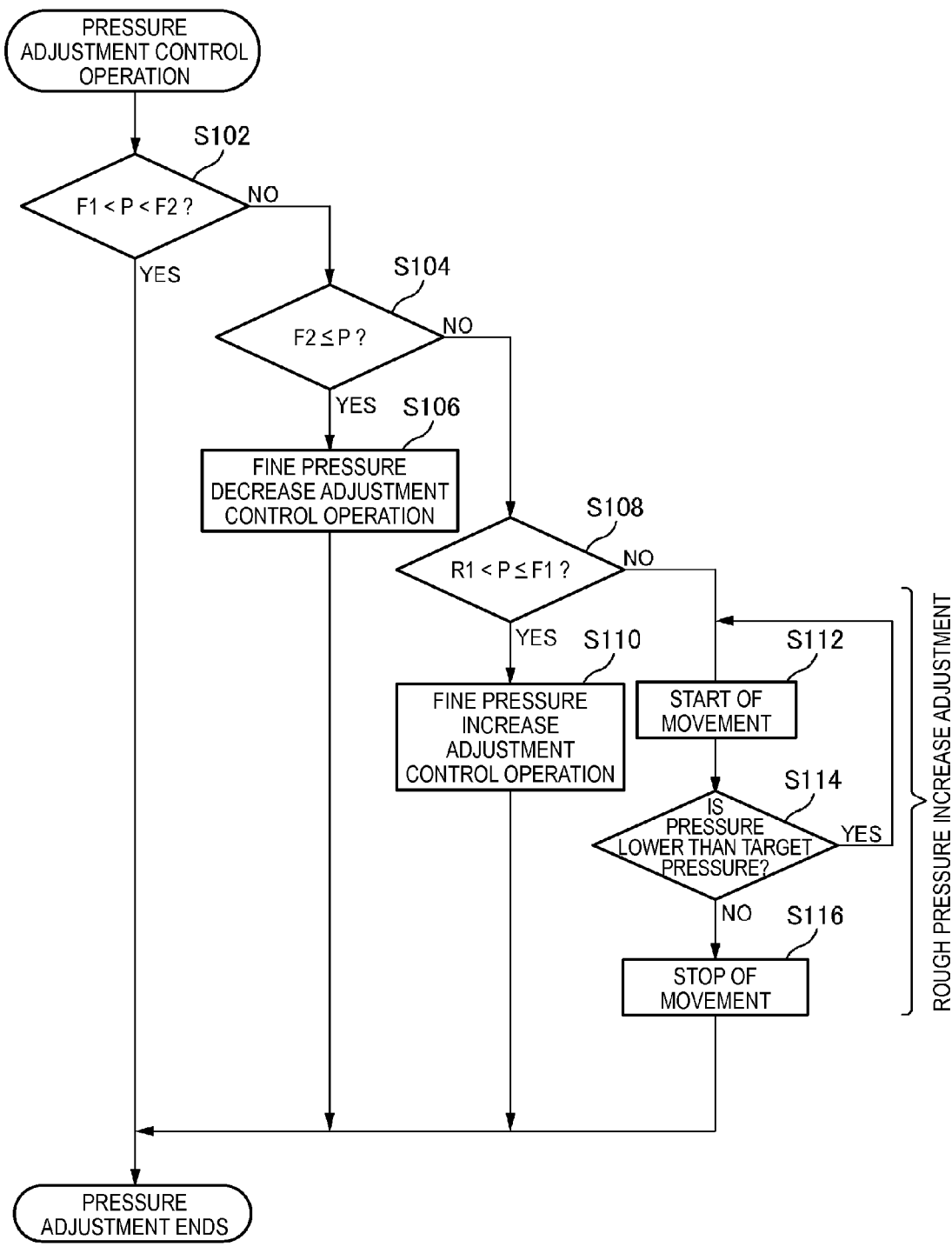
FIG. 8 is a flowchart of a pressure adjustment control operation.

FIG. 8 is a flowchart of the pressure adjustment control operation. When the pulsation generator start-up switch is not pushed, the pressure adjustment control operation is performed every 20 ms.

The pump control unit 710 determines whether the pressure P of the fluid container 760 is higher than the pressure F1 and is lower than the pressure F2 (S102). When the pressure P is higher than the pressure F1 and is lower than the pressure F2, the pressure adjustment control operation ends. As such, when the pressure P is higher than the pressure F1 and is lower than the pressure F2, the pressure adjustment control operation is not performed, and thereby it is possible to prevent the pressure control operation from being uselessly performed, and to prevent an increase in pressure change.

In contrast, in step S102, when it is not satisfied that the pressure P is higher than the pressure F1 and is lower than the pressure F2, the pump control unit 710 determines whether the pressure P is the pressure F2 or higher (S104). When the pressure P is the pressure F2 or higher, the pump control unit 710 performs the fine pressure decrease adjustment control operation (S106).

Hereinafter, the fine pressure decrease adjustment control operation will be described. The pump control unit 710 according to the embodiment can control the motor 730 to continuously move the slider 720 at a predetermined speed, and can control the motor 730 to move the slider 720 by a very small distance. The motor 730 is controlled to rotate by a minimum unit so as to move the slider 720 by the very small distance. In the fine pressure decrease adjustment control operation, the pump control unit 710 moves the slider 720 toward the second limit sensor 744 by the very small distance. As a result, due to the inner pressure of the fluid container 760, the plunger 762 moves by the very small distance in an increase direction of the inner volume of the fluid accommodation portion 765. Accordingly, the inner pressure of the fluid container 760 decreases by a very small amount of pressure.

In step S104, when the pressure P is not the pressure F2 or higher, the pump control unit 710 determines whether the pressure P is higher than the pressure R1 and is the pressure F1 or lower (S108). When the pressure P is higher than the pressure R1 and is the pressure F1 or lower, the pump control unit 710 performs the fine pressure increase adjustment control operation (S110).

Hereinafter, the fine pressure increase adjustment control operation will be described. In the fine pressure increase adjustment control operation, the pump control unit 710 moves the slider 720 toward the first limit sensor 741 by a very small distance. The plunger 762 moves in a decrease direction of the inner volume of the fluid accommodation portion 765 of the fluid container 760. Accordingly, the inner pressure of the fluid container 760 increases by a very small amount of pressure.

In step S108, when it is not satisfied that the pressure P is higher than the pressure R1, and is the pressure F1 or lower, the pump control unit 710 performs the rough pressure increase adjustment control operation (S112 to S116). In the rough pressure increase adjustment control operation, the pump control unit 710 controls the motor 730 to continuously move the slider 720 toward the first limit sensor 741. Subsequently, the pump control unit 710 determines whether the pressure P is lower than the target pressure Pt (S114). When the pressure P is lower than the target pressure Pt, the pump control unit 710 controls the motor 730 to continuously move the slider 720 toward the limit sensor 741 again. In contrast, in step S114, when the pressure P is the target pressure Pt or higher, the pump control unit 710 ends the movement of the slider 720. As such, the pressure adjustment control operation ends.

First, as illustrated in FIG. 7, the rough pressure increase adjustment operation is performed in the execution of the above-mentioned pressure adjustment control operation. Accordingly, the pressure P rapidly increases to approximately the target pressure Pt. When the pressure P increases to the target pressure, the rough pressure increase adjustment control operation ends. While the pressure P is between the pressure F1 and the pressure F2, a particular pressure adjustment operation is not performed.

Thereafter, the pressure P decreases gradually due to the gasket 763. When the pressure P decreases to the pressure F1 or lower, the fine pressure increase adjustment operation is performed. Since the fine pressure increase adjustment control operation is performed so as to move the slider 720 by the very small distance, and to increase the pressure by the very small amount of pressure as described above, the pressure P stays at approximately the target pressure Pt.

When the pressure P exceeds the pressure F1, the pressure control operation is stopped. Accordingly, due to the gasket 763, the pressure P decreases gradually again. Thereafter, similarly as described above, the fine pressure increase adjustment operation is performed. These processes are repeated, and thereby the pressure P is stabilized at approximately the target pressure Pt.

The reason that the pressure adjustment control operation is performed as described above is as follows. That is, when the pressure P is the pressure R1 or lower, it is necessary to rapidly increase the pressure P to approximately the target pressure Pt from a pressure at which the fluid cannot be properly ejected. For this reason, when the pressure P is the pressure R1 or lower, the pump control unit 710 rapidly increases the pressure via the rough pressure increase adjustment control operation.

When the pressure P is higher than the pressure R1, and is the pressure F1 or lower, the pressure has already increased to a level in which the fluid can be ejected. For this reason, the pressure may increase by a very small amount of pressure absorbed by the gasket 763. Accordingly, when the pressure P is higher than the pressure R1, and is the pressure F1 or lower, the pressure is finely adjusted via the fine pressure increase adjustment control operation.

When the pressure P is higher than the pressure F1 and is lower than the pressure F2, the pressure P is very close to the target pressure Pt. When the pump control unit 710 controls the inner pressure of the fluid container 760 containing the gasket 763 in high friction contact with the syringe 761, a control delay may occur, and the pressure may be severely changed during the adjustment control operation of the pressure P. Accordingly, when the pressure P is higher than the pressure F1 and is lower than the pressure F2, the pressure control operation is stopped.

In this manner, it is possible to rapidly increase the pressure P to the target pressure Pt, and after the pressure P increases to approximately the target pressure Pt, it is possible to maintain the pressure P at approximately the target pressure Pt via the fine pressure increase adjustment control operation. Since it is possible to maintain the pressure P at approximately the target pressure Pt immediately before the fluid is ejected, when there is a demand for the ejection of the fluid present, it is possible to immediately send the fluid to the pulsation generator 100 at a proper pressure.

Subsequently, the ejection control operation will be described.

Figure 9:
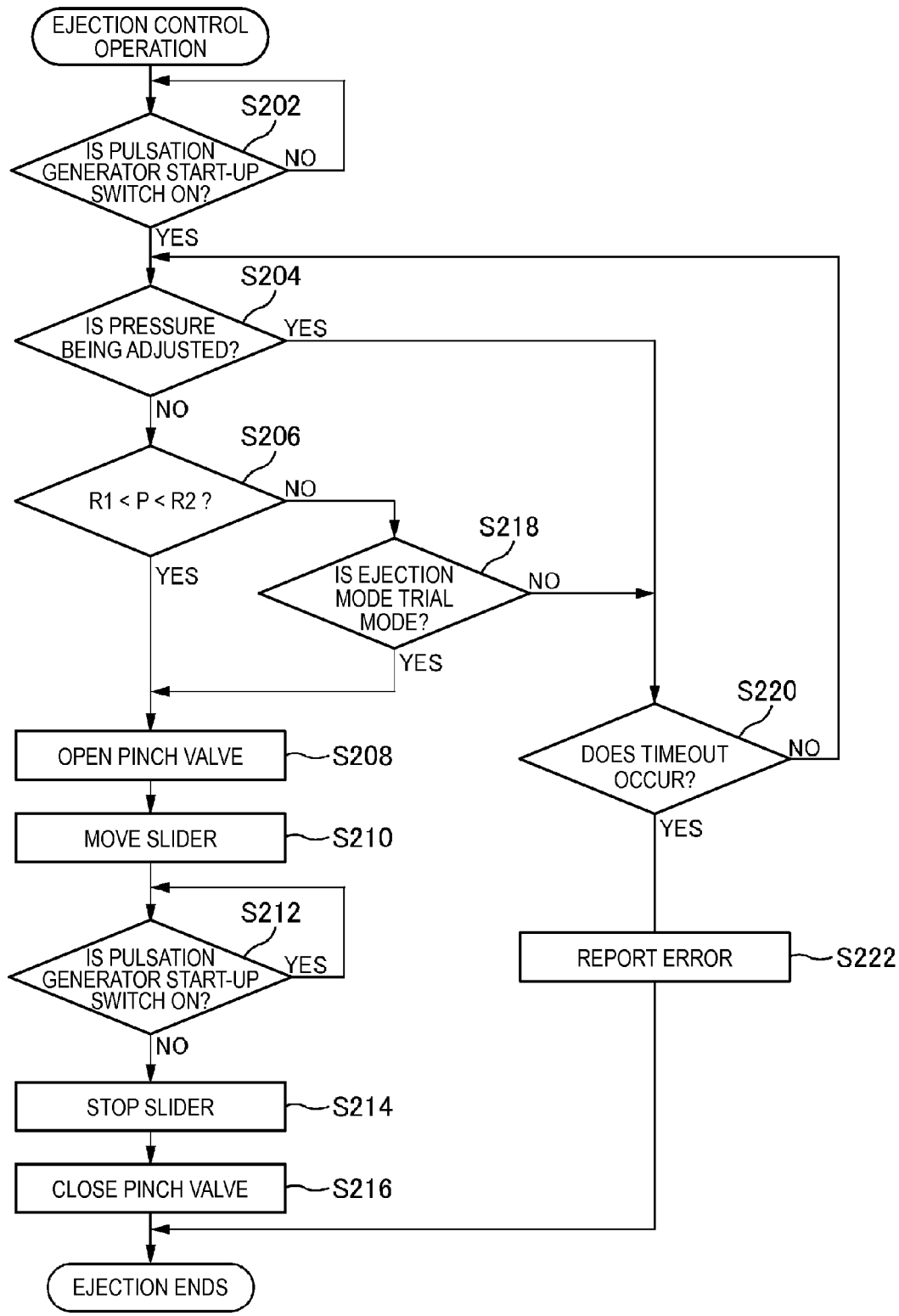
FIG. 9 is a flowchart of an ejection control operation.

FIG. 9 is a flowchart illustrating the ejection control operation.

The drive control unit 600 determines whether the pulsation generator start-up switch (not illustrated) is turned on (S202). The pulsation generator start-up switch is a unit such as a foot switch that is connected to the drive control unit 600, and outputs a demand for the ejection of the fluid to the drive control unit 600 when the pulsation generator start-up switch is turned on. In step S202, when the pulsation generator start-up switch is not turned on, the drive control unit 600 re-determines whether the pulsation generator start-up switch is turned on. Accordingly, a loop for waiting for the turning on of the pulsation generator start-up switch is established.

In step S202, when the pulsation generator start-up switch is turned on, the drive control unit 600 inquires of the pump control unit 710 whether the pressure adjustment control operation is performed (S204). When the pressure adjustment control operation is performed, the drive control unit 600 determines whether timeout occurs (S220). The timeout indicates when 500 ms has elapsed after the pulsation generator start-up switch is turned on and then the count up starts.

When the timeout does not occur, the drive control unit 600 performs step S204 again. In contrast, when the timeout occurs, the drive control unit 600 reports an error (S222). In regard to a technique of reporting an error, it is possible to display a message indicative of an occurrence of an error on a display device (not illustrated), or to generate a sound indicative of an occurrence of an error.

In step S204, when it is determined that the pressure adjustment control operation is not performed, the drive control unit 600 determines whether the pressure P is higher than the pressure R1 and is lower than the pressure R2 (S206). In step S206, when it is not satisfied that the pressure P is higher than the pressure R1 and is lower than the pressure R2, the drive control unit 600 determines whether the fluid ejection device 1 is in a trial mode (S218).

The fluid ejection device 1 according to the embodiment has two ejection modes such as a normal mode (equivalent to a first ejection mode) and the trial mode (equivalent to the second ejection mode). In the normal mode, the fluid is allowed to be ejected only when the pressure P is higher than the pressure R1 and is lower than the pressure R2. In contrast, in a case where the ejection mode is set to the trial mode, even when it is not satisfied that the pressure P is higher than the pressure R1 and is lower than the pressure R2, the fluid is allowed to be ejected.

As such, it is possible to eject the fluid at a proper pressure by using the fluid ejection device 1 in the normal mode during an operation, and in contrast, it is possible to confirm a fluid ejection operation of the fluid ejection device 1 by using the fluid ejection device 1 in the trail mode.

For example, in regard to a technique of switching the ejection mode, it is possible to switch the ejection mode between the normal mode and the trial mode via a switch (not illustrated). The ejection mode may be automatically switched to the trial mode immediately after the ejection intensity switching switch is switched. The ejection mode may be automatically switched to the trial mode immediately after the deaeriation process (flushing operation) is performed. The ejection mode may be automatically switched to the trial mode immediately after the priming operation is performed.

The ejection mode may be automatically switched to the trial mode in response to the pressure P. That is, the ejection mode may be automatically switched to the trial mode when it is not satisfied that the pressure P is higher than the pressure R1 and is lower than the pressure R2.

In step S218, when it is determined that the ejection mode is not the trial mode, step S220 is executed.

In contrast, in step S218, when it is determined that the ejection mode is the trial mode, or in step S206, when it is determined that the pressure P is higher than the pressure R1 and is lower than the pressure R2, the drive control unit 600 instructs the pump control unit 710 to open the pinch valve 750 (S208). The pump control unit 710 moves the slider 720 in a direction in which the plunger 762 is pushed at substantially the same time as when the pinch valve 750 is opened.

Subsequently, the drive control unit 600 determines whether the pulsation generator start-up switch is continuously turned on (S212). When the pulsation generator start-up switch is continuously turned on, the process returns to step S212 again. This loop is repeated, and thereby it is possible to send the fluid to the pulsation generator 100 and to eject the fluid from the pulsation generator 100.

When the fluid is ejected in step S212, and the ejection mode is the trial mode, a message indicative of the trial mode is reported via a reporting device (not illustrated). In regard to a reporting technique via the reporting device, it is possible to display a message indicative of the trial mode, or to generate a predetermined alarm sound.

In step S212, when the pulsation generator start-up switch is turned off, the drive control unit 600 instructs the pump control unit 710 to stop the movement of the slider 720 (S214). At substantially the same time, the drive control unit 600 instructs the pump control unit 710 to close the pinch valve 750 (S216). Accordingly, the control of the ejection of the fluid is completed.

In a case where the ejection mode is the normal mode, when the pump 700 is controlled in order for the pressure P to approach the target pressure Pt, and the pressure P is higher than the pressure R1, the drive control unit 600 receives a demand for the ejection of the fluid, and thereby it is possible to reduce an amount of time taken from the reception of the demand for the ejection of the fluid to the ejection of the fluid.

In contrast, in a case where the ejection mode is the trial mode, even when the pump 700 is controlled in order for the pressure P to approach the target pressure Pt, and the pressure P is not closer to the target pressure Pt than the pressure R1, the drive control unit 600 receives a demand for the ejection of the fluid, and thereby it is possible to eject the fluid in the trial mode.

Another Embodiment

In the example of the embodiment, the fluid ejection device 1 is applied to an operation scalpel used to incise or excise living tissue; however, the invention is not limited to the embodiment, and can be applied to other medical tools for excision, cleaning, or the like. Specifically, the fluid ejection device 1 can be used to clean a fine object or structure.

In the embodiment, the fluid is ejected by using the piezoelectric element; however, a laser bubble method may be adopted by which a fluid in a pressure chamber is powerfully ejected by generating bubbles in the fluid in the pressure chamber with a laser beam. A heater bubble method may be adopted by which a fluid in a pressure chamber is powerfully ejected by generating bubbles in the fluid in the pressure chamber with a heater.

In the embodiment, the fluid is ejected in the form of a pulsed flow; however, the fluid may be continuously ejected. When the fluid container 760 is formed of an infusion solution bag that accommodates a fluid, it is possible to perform the rough pressure increase adjustment control operation, the fine pressure increase adjustment control operation, and the fine pressure decrease adjustment control operation as follows. That is, in the rough pressure increase adjustment control operation, air is pressure-fed to the pressurized chamber 800 by continuously operating the compressor 810. In the fine pressure increase adjustment control operation, air is pressure-fed to the pressurized chamber 800 by operating the compressor 810 for a very small amount of time. In the fine pressure decrease adjustment control operation, the pressure of the pressurized chamber 800 decreases by a very small amount of pressure by opening the air vent valve 812 for a very small amount of time.

The embodiment is given to help understanding the invention, and the interpretation of the invention is not limited to the embodiment. Modifications or improvements can be made to the invention insofar as the modifications or the improvements do not depart from the spirit of the invention, and the invention includes the equivalent.

What is claimed is:

1. A fluid ejection device comprising:
   a fluid ejection unit that ejects a fluid;
   an ejection control unit that controls the ejection of the fluid from the fluid ejection unit;
   a fluid container that accommodates the fluid to be supplied to the fluid ejection unit; and
   a pressure adjustment unit that adjusts an inner pressure of the fluid container in such a manner that the inner pressure of the fluid container gets closer to a target pressure than a first threshold value for the inner pressure of the fluid container,
   wherein the ejection control unit has a first ejection mode and a second ejection mode as ejection modes, and in the first ejection mode, when the inner pressure of the fluid container is closer to the target pressure than a second threshold value separated from the target pressure further than the first threshold value, the ejection control unit receives a demand for the ejection of the fluid, and in the second ejection mode, even when the inner pressure of the fluid container is not closer to the target pressure than the second threshold value, the ejection control unit receives a demand for the ejection of the fluid.

2. The fluid ejection device according to claim 1, further comprising
a reporting device configured to report that the ejection control unit receives a demand for the ejection of the fluid in the second ejection mode.

3. The fluid ejection device according to claim 1, further comprising
a switch that switches an ejection mode between the first ejection mode and the second ejection mode.

4. The fluid ejection device according to claim 1,
wherein when the inner pressure of the fluid container is not closer to the target pressure than the second threshold value, the ejection mode is switched to the second ejection mode.

5. The fluid ejection device according to claim 1,
wherein after at least one of an operation of filling the fluid ejection unit with the fluid, a deaeration operation of the fluid ejection unit, and a fluid ejection intensity change operation of the fluid ejection unit is performed, the ejection mode is switched to the second ejection mode.

6. The fluid ejection device according to claim 1,
wherein in a state where the inner pressure of the fluid container is lower than the target pressure, when the inner pressure of the fluid container is separated from the target pressure by the second threshold value or greater, the pressure adjustment unit performs a first pressure increase control operation in which the pressure adjustment unit increases the inner pressure by reducing the inner volume of the fluid container by a first amount, and when the inner pressure of the fluid container is closer to the target pressure than the second threshold value, and is separated from the target pressure by the first threshold value or greater, the pressure adjustment unit performs a second pressure increase control operation in which the pressure adjustment unit increases the inner pressure by reducing the inner volume of the fluid container by a second amount less than the first amount.

7. The fluid ejection device according to claim 1, further comprising:
a connection channel that connects the fluid ejection unit and the fluid container, and acts as a channel through which the fluid flows; and
an opening and closing unit that is controlled to open and close the connection channel by the pressure adjustment unit,
wherein when the ejection control unit receives a demand for the ejection of the fluid, the pressure adjustment unit controls the opening and closing unit to open the connection channel, and stops the adjustment of the inner pressure of the fluid container.

8. The fluid ejection device according to claim 7,
wherein when the ejection control unit receives a demand for the ejection of the fluid, the pressure adjustment unit supplies the fluid to the fluid ejection unit by controlling the opening and closing unit to open the connection channel and reducing the inner volume of the fluid container by a predetermined amount each time.

* * * * *